United States Patent
Sakai et al.

(12)

(10) Patent No.: US 6,197,961 B1
(45) Date of Patent: Mar. 6, 2001

(54) PROCESS FOR PREPARING ACID SALTS OF γ-(PIPERIDYL)BUTYRIC ACID

(75) Inventors: Toshito Sakai, Yawata; Masayo Nagaoka, Osaka; Ken Kanno, Itano-gun, all of (JP)

(73) Assignee: Koei Chemical Co., Ltd., Osaka (JP)

( * ) Notice: Subject to any disclaimer, the term of this patent is extended or adjusted under 35 U.S.C. 154(b) by 0 days.

(21) Appl. No.: 09/077,316

(22) PCT Filed: Oct. 7, 1997

(86) PCT No.: PCT/JP97/03594

§ 371 Date: Jan. 4, 1998

§ 102(e) Date: Jan. 4, 1998

(87) PCT Pub. No.: WO98/15531

PCT Pub. Date: Apr. 16, 1998

(30) Foreign Application Priority Data

Oct. 7, 1996 (JP) .................................................. 8-286119

(51) Int. Cl.[7] .................................................. C07D 211/30
(52) U.S. Cl. .................................................. 546/248
(58) Field of Search .................................................. 546/248

(56) References Cited

U.S. PATENT DOCUMENTS

| 3,875,171 | * | 4/1975 | Gutzwiller et al. | ............. | 260/293.88 |
| 4,012,396 | * | 3/1977 | Grethe et al. | ................... | 260/293.77 |
| 4,433,152 | | 2/1984 | Muramatsu et al. | . | |

FOREIGN PATENT DOCUMENTS

| 0 718 287 A2 | 6/1996 | (EP) . |
| 1 270 061 | 4/1972 | (GB) . |
| 57-193456 | 11/1982 | (JP) . |
| WO 96/28425 | 9/1996 | (WO) . |

OTHER PUBLICATIONS

Chem. abstr., vol. 58, No. 9, Apr. 29, 1963, col. 9024g–9025d, particularly abstract of col. 9024h, Mikhlina, E.E. et al., "Synthesis of 1–azabicyclo (3.2.2) nonane–2–carboxylic acid", Zh. Obshch. Khim. 1962, vol. 32, p. 2177–2184.

Journal of the American Chemical Society, vol. 69, No. 10, pp. 2461–2466, Oct. 1947.

Doering W E et al., "Electrophilic Reactions of 2– and 4–Vinylpyridines", Journal of the American Chemical Society, vol. 69, pp.2461–2466 (Oct. 1, 1947).

* cited by examiner

*Primary Examiner*—John Kight
*Assistant Examiner*—Raymond Covington
(74) *Attorney, Agent, or Firm*—Armstrong, Westerman, Hattori, McLeland & Naughton

(57) ABSTRACT

At least one of a Rh catalyst, a Pd catalyst or a Ru catalyst is used as a catalyst in preparing the salt of γ-(piperidyl)-butyric acid (2) by hydrogenating the salt of γ-(pyridyl) butyric acid (1) [preferably the salt of γ-(pyridyl)butyric acid (1) obtained in the undermentioned steps (a) and (b) and containing not more than 3% by weight of salt of bis (pyridylethyl)acetic acid (3)] in a solvent in the presence of a catalyst:

(a) reacting the vinylpyridine (4) with the diester of malonic acid (5) in the presence of a base to give the 2-(pyridylethyl)malonic acid diester (6), and (b) hydrolyzing and decarboxylating the 2-(pyridylethyl) malonic acid diester (6) obtained in the step (a) in an acidic aqueous solution to give the salt of γ-(pyridyl) butyric acid (1).

11 Claims, No Drawings

PROCESS FOR PREPARING ACID SALTS OF γ-(PIPERIDYL)BUTYRIC ACID

FIELD OF THE INVENTION

The present invention relates to a novel process for preparing a salt of γ-(piperidyl)butyric acid with an acid, the salt being represented by the formula (2)

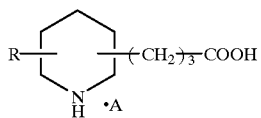

(2)

wherein R is a hydrogen atom or an alkyl group, and A is an acid [hereinafter referred to as "salt of γ-(piperidyl)butyric acid (2)"].

The salt of γ-(piperidyl)butyric acid (2) is a compound which is useful as an intermediate for a pharmaceutical chemical by itself or in the form of a γ-(piperidyl)butyric acid liberated from the acid.

BACKGROUND OF THE INVENTION

The salt of γ-(piperidyl)butyric acid (2) can be prepared by hydrogenating a salt of γ-(2-pyridyl)butyric acid with an acid for conversion of the pyridine ring to a piperidine ring. It is known to prepare the salt of γ-(piperidyl)butyric acid (2) by hydrogenating a salt of (γ-pyridyl)butyric acid with an acid using a platinum oxide as a catalyst [J. Am. Chem. Soc., 69,2461 (1947)].

However, the above-mentioned conventional process hydrogenates the salt of γ-(2-pyridyl)butyric acid with an acid at a concentration of 2% in the reaction mixture, namely a much diluted salt, consequently leading to a low reactor efficiency and a low productivity. Thus the process is not practical.

The above-mentioned process poses a further problem of necessitating a large amount of platinum oxide as the catalyst. The foregoing publication teaches the use of platinum oxide in an amount of as large as 4.3% by weight in terms of Pt based on a γ-(2-pyridyl)butyric acid hydrochloride.

No investigation has been heretofore made about the use of other catalysts than platinum oxide for the hydrogenation of a salt of γ-(pyridyl)butyric acid with an acid. It is an object of the present invention to provide a catalyst capable of hydrogenating a salt of γ-(pyridyl)butyric acid with an acid to efficiently convert the pyridine ring to a piperidine ring, providing a process for preparing a salt of γ-(piperidyl)butyric acid (2) with a high productivity.

DISCLOSURE OF THE INVENTION

The present inventors conducted extensive research to overcome the foregoing prior art problems and made the following findings about the catalyst and raw materials useful in preparing a salt of γ-(piperidyl)butyric acid (2). The present invention was completed based on the novel findings.

<Catalyst>

When a Rh catalyst, a Pd catalyst or a Ru catalyst is used as the catalyst in hydrogenating a salt of γ-(pyridyl)butyric acid with an acid, the salt thereof being represented by the formula (1)

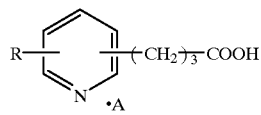

(1)

wherein R is a hydrogen atom or an alkyl group, and A is an acid [hereinafter referred to as "salt of γ-(pyridyl)butyric acid (1)"], the salt of γ-(piperidyl)butyric acid (2) can be prepared in a relatively short time with a high productivity. When these catalysts are used, unexpectedly the hydrogenation of salt of γ-(pyridyl)butyric acid (1) is completed in a short time even at a very low hydrogen pressure as compared with the hydrogenation of a free γ-(pyridyl)butyric acid.

<Raw Materials>

The salt of γ-(pyridyl)butyric acid (1) can be prepared by carrying out the steps of:

(a) reacting a vinylpyridine compound represented by the formula (4)

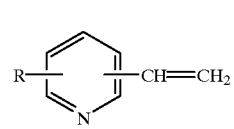

(4)

wherein R is as defined above [hereinafter referred to as "vinylpyridine (4)"] with a diester of malonic acid represented by the formula (5)

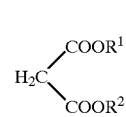

(5)

wherein $R^1$ and $R^2$ are the same or different and each represents an alkyl group [hereinafter referred to as "diester of malonic acid (5)"] in the presence of a base to give a diester of 2-(pyridylethyl)malonic acid represented by the formula (6)

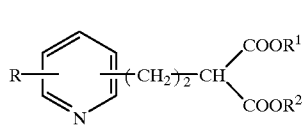

(6)

wherein R, $R^1$ and $R^2$ are as defined above [hereinafter referred to as "2-(pyridylethyl)malonic acid diester (6)"], and (b) hydrolyzing and decarboxylating the 2-(pyridylethyl)malonic acid diester (6) prepared in the step (a) in an acidic aqueous solution.

When the salt of γ-(piperidyl)butyric acid (2) is prepared by hydrogenation of the salt of γ-(pyridyl)butyric acid (1) obtained in the steps (a) and (b), the specific impurities present in the salt of γ-(pyridyl)butyric acid (1) adversely affect the reaction time for hydrogenation and the purity of the obtained salt of γ-(piperidyl)butyric acid (2).

Stated more specifically, the process of preparing the salt of γ-(pyridyl)butyric acid (1) produces, as a by-product, a salt of bis(pyridylethyl)acetic acid with an acid, the salt thereof being represented by the formula (3)

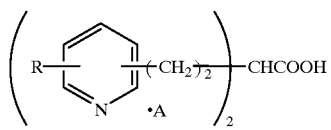

wherein R and A are as defined above [hereinafter referred to as "salt of bis(pyridylethyl)acetic acid (3)"].

When the salt of γ-(pyridyl)butyric acid (1) containing the salt of bis(pyridylethyl)acetic acid (3) is hydrogenated, the reaction tends to involve a longer time and a high-purity salt of γ-(piperidyl)butyric acid (2) is difficult to produce.

If not more than 3% by weight of the salt of bis (pyridylethyl)acetic acid (3) is present in the salt of γ-(pyridyl)butyric acid (1), the hydrogenation is completed in a very short time and a high-purity salt of γ-(piperidyl) butyric acid (2) can be easily produced.

SUMMARY OF THE INVENTION

According to the present invention, there is provided a process for preparing the salt of γ-(piperidyl)butyric acid (2), the process comprising the step of hydrogenating the salt of γ-(pyridyl)butyric acid (1) [preferably the salt of γ-(pyridyl) butyric acid (1) obtained by carrying out the undermentioned steps (a) and (b) and containing not more than 3% by weight of salt of bis(pyridylethyl)acetic acid (3)] in a solvent in the presence of a catalyst, the process being characterized in that the catalyst is a Rh catalyst, a Pd catalysts or a Ru catalyst:

(a) reacting the vinylpyridine (4) with the diester of malonic acid (5) in the presence of a base to give the 2-(pyridylethyl)malonic acid diester (6), and (b) hydrolyzing and decarboxylating the 2-(pyridylethyl) malonic acid diester (6) obtained in the step (a) in an acidic aqueous solution to give the salt of γ-(pyridyl)butyric acid (1).

According to the present invention, the salt of γ-(piperidyl)butyric acid (2) can be prepared in a relatively short time with a high productivity. Especially if the salt of γ-(pyridyl)butyric acid (1) to be hydrogenated is one prepared in the steps (a) and (b) and containing not more than 3% by weight of salt of bis(pyridylethyl)acetic acid (3), the hydrogenation is completed in a shorter time and a high-purity salt of γ-(piperidyl)butyric acid (2) can be easily prepared.

BEST MODE FOR CARRYING OUT THE INVENTION

Salt of γ-(pyridyl)butyric acid (1)

The salt of γ-(piperidyl)butyric acid (2) can be prepared by hydrogenation of the salt of γ-(pyridyl)butyric acid (1). R in the formula (1) representing the salt of γ-(pyridyl)butyric acid (1) is a hydrogen atom or an alkyl group. Preferred alkyl group is a lower alkyl group having 1 to 4 carbon atoms. A in the formula (1) is an acid. Examples of the acid are mineral acids such as hydrochloric acid and sulfuric acid, and organic acids such as p-toluenesulfonic acid and trifluoromethanesulfonic acid.

Specific examples of the salt of γ-(pyridyl)butyric acid (1) are salts of γ-(pyridyl)butyric acids with other acids. Useful γ-(pyridyl)butyric acids include, for example, γ-(2-pyridyl) butyric acid, γ-(3-pyridyl)butyric acid, γ-(4-pyridyl)butyric acid, γ-(5-methyl-2-pyridyl)butyric acid, γ-(6-methyl-2-pyridyl)butyric acid, γ-(4-methyl-3-pyridyl)butyric acid, γ-(2-methyl-5-pyridyl)butyric acid, γ-(5-ethyl-2-pyridyl) butyric acid, etc. Examples of other acids include hydrochloric acid, sulfuric acid and like mineral acids, p-toluenesulfonic acid, trifluoro-methanesulfonic acid and like organic acids.

Preparation of salt of γ-(pyridyl)butyric acid (1)

The salt of γ-(pyridyl)butyric acid (1) can be prepared by conventional processes. For example, it can be prepared by hydrolysis and decarboxylation of 2-(pyridylethyl)malonic acid diester (6) in an acidic aqueous solution (step (b)). The 2-(pyridylethyl)malonic acid diester (6) can be produced as by reacting the vinylpyridine (4) with the diester of malonic acid (5) in the presence of a base (step (a)).

<Step (a)>

The reaction in the step (a) is so-called "Michael addition reaction". Examples of the vinylpyridine (4) are 2-vinylpyridine, 3-vinylpyridine, 4-vinylpyridine, 5-methyl-2-vinylpyridine, 6-methyl-2-vinylpyridine, 4-methyl-3-vinylpyridine, 2-methyl-5-vinylpyridine, 5-ethyl-2-vinylpyridine and the like.

$R^1$ and $R^2$ in the formula (5) representing the diester of malonic acid (5) are the same or different and each represents an alkyl group. Preferred alkyl group is a lower alkyl group having 1 to 4 carbon atoms. Examples of the diester of malonic acid (5) are dimethyl malonate, diethyl malonate, dipropyl malonate, diisopropyl malonate, dibutyl malonate and diisobutyl malonate.

The 2-(pyridylethyl)malonic acid diester (6) can be efficiently formed when the diester of malonic acid (5) is used in an amount of at least 1 mole, preferably 1 to 3 moles, more preferably 1.5 to 2.5 moles, per mole of the vinylpyridine (4). If the amount of diester of malonic acid (5) used is less than 1 mole per mole of the vinylpyridine (4), the reaction is likely to produce by-products.

Useful bases include those conventionally used in the Michael addition reaction. Preferred base is alkali metal alkoxide. Examples of the alkali metal alkoxide are methoxide, ethoxide, propoxide, isopropoxide, 2-methyl-1-propoxide or 2-methyl-2-propoxide of lithium, sodium, potassium or cesium.

The reaction efficiently proceeds when the base is used in an amount of 0.05 to 1 mole, preferably 0.1 to 0.5 mole, per mole of the vinylpyridine (4). The amount of the base less than the above range is responsible for an extended reaction time, whereas the amount thereof exceeding the above range is liable to result in the formation of by-products.

The Michael addition reaction in the step (a) can be carried out in a solvent. Useful solvents are, for example, alcohols and the like. Examples of the alcohol are alcohols having 1 to 4 carbon atoms such as methyl alcohol, ethyl alcohol, propyl alcohol, isopropyl alcohol, 2-methyl-1-propyl alcohol and the like. The amount of the solvent used is 0.1 to 2 parts by weight, preferably 0.3 to 1 part by weight, per part by weight of the vinylpyridine (4).

The Michael addition reaction in the step (a) can be conducted, for example, by adding dropwise the vinylpyridine (4) over a period of 0.5 to 2 hours to a mixture of a base, the diester of malonic acid (5) and optionally a solvent with stirring at 75 to 110° C. After dropwise addition of vinylpyridine (4), the mixture may be maintained at the same temperature for 2 to 8 hours to complete the reaction, giving 2-(pyridylethyl)malonic acid diester (6) in a high yield.

<Step (b)>

The salt of γ-(pyridyl)butyric acid (1) can be prepared by hydrolyzing and decarboxylating the 2-(pyridylethyl) malonic acid diester (6) in an acidic aqueous solution at the step (b).

For example, the salt of γ-(pyridyl)butyric acid (1) can be prepared by hydrolyzing and decarboxylating the reaction mixture obtained in the step (a) and containing the 2-(pyridylethyl)malonic acid diester (6), or by hydrolyzing and decarboxylating the purified 2-(pyridylethyl)malonic acid diester (6) isolated from the reaction mixture obtained at the step (a).

Examples of the acidic aqueous solution are aqueous solutions of acids such as hydrochloric acid, sulfuric acid and like mineral acids, p-toluenesulfonic acid, trifluoromethanesulfonic acid and like organic acids.

The hydrolysis and decarboxylation can be efficiently carried out when the acid (acidic aqueous solution) is used in an amount sufficient to acidify the mixed solution comprising the 2-(pyridylethyl)malonic acid diester (6) and the acidic aqueous solution.

For example, when hydrolyzing and decarboxylating the purified 2-(pyridylethyl)malonic acid diester (6) isolated from the reaction mixture after Michael addition reaction in the step (a), at least one equivalent, preferably 1.1 to 2 equivalents, of the acid is used relative to the 2-(pyridylethyl)malonic acid diester (6).

In hydrolyzing and decarboxylating the reaction mixture resulting from the Michael addition reaction in the step (a), one equivalent, preferably 1.1 to 2 equivalents, of the acid is used relative to the total amount of 2-(pyridylethyl) malonic acid diester (6) and the base used in the Michael addition reaction, both contained in the reaction mixture.

The hydrolysis and decarboxylation in the step (b) can be performed, for example, by mixing the 2-(pyridylethyl) malonic acid diester (6) and the acidic aqueous solution and maintaining the mixture with stirring at 60 to 120° C., preferably 90 to 110° C. for 8 to 12 hours. After completion of the reaction, the reaction mixture is concentrated, the precipitate is separated by filtration and the filtrate is cooled, giving crystals of salt of γ-(pyridyl)butyric acid (1).

<Purification of salt of γ-(pyridyl)butyric acid (1)>

In the Michael addition reaction at the step (a), a side reaction occurs to react 2 molecules of vinylpyridine (4) with one molecule of diester of malonic acid (5), producing a diester of 2,2-bis(pyridylethyl)malonic acid represented by the formula (7)

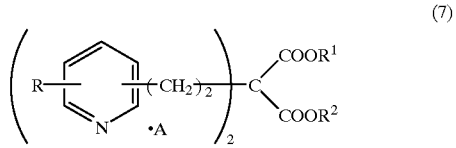

(7)

wherein R, $R^1$ and $R^2$ are as defined above (hereinafter referred to as "2,2-bis(pyridylethyl)malonic acid diester (7)"). The 2,2-bis(pyridylethyl)malonic acid diester (7) is hydrolyzed and decarboxylated in the step (b), whereby the salt of bis(pyridylethyl)acetic acid (3) is produced.

The 2-(pyridylethyl)malonic acid diester (6) isolated by distillation from the reaction mixture after the Michael addition reaction in the step (a) is hydrolyzed and decarboxylated, thereby producing the salt of γ-(pyridyl) butyric acid (1) free of the salt of bis(pyridylethyl)acetic acid (3).

When the crystals of salt of γ-(pyridyl)butyric acid (1) obtained in the step (b) contain the salt of bis(pyridylethyl) acetic acid (3), desirably the concentration of the salt of bis(pyridylethyl)acetic acid (3) is reduced to not more than 3% by weight.

The crystals of salt of γ-(pyridyl)butyric acid (1) containing the salt of bis(pyridylethyl)acetic acid (3) can be purified by recrystallization. In the recrystallization of salt of γ-(pyridyl)butyric acid (1), water, alcohol, an aqueous solution of a mineral acid or mixtures thereof can be used as a solvent.

Preparation of salt of γ-(piperidyl)butyric acid (2)

<Hydrogenation of salt of γ-(pyridyl)butyric acid (1)>

When the salt of γ-(pyridyl)butyric acid (1) is hydrogenated for conversion of the pyridine ring to a piperidine ring, the corresponding salt of γ-(piperidyl)butyric acid (2) can be prepared. When the salt of γ-(pyridyl)butyric acid (1) containing not more than 3% by weight of salt of bis (pyridylethyl)acetic acid (3) is hydrogenated, a high-purity salt of γ-(piperidyl)butyric acid (2) can be easily formed in a short time.

A salt formed from a free γ-(pyridyl)butyric acid and an acid is usable as the salt of γ-(pyridyl)butyric acid (1). The salt of γ-(piperidyl)butyric acid (2) can also be prepared by mixing an acid and a γ-(pyridyl)butyric acid, followed by hydrogenation of the mixture instead of hydrogenation of the salt of γ-(pyridyl)butyric acid (1).

<Catalyst>

Useful catalysts include Rh catalysts, Pd catalysts or Ru catalysts. Using a Rh catalyst or a Pd catalyst, the salt of γ-(pyridyl)butyric acid (1) can be hydrogenated under milder conditions in a shorter time for conversion of the pyridine ring to a piperidine ring.

Examples of useful Rh catalysts, Pd catalysts or Ru catalysts include catalysts having Rh, Pd or Ru supported on a carrier. Useful carriers are, for example, carbon, alumina and the like among which carbon is preferred and active carbon is especially preferred. When a catalyst having one of Rh, Pd or Ru supported on a carrier is used, the amount of Rh, Pd or Ru to be supported on the carrier is not limited, but usually it is 1 to 10% by weight based on the carrier.

If the amount of a Rh catalyst, a Pd catalyst or a Ru catalyst used is at least 0.05% by weight (preferably 0.05 to 0.3% by weight from the economical viewpoint) calculated as Rh, Pd or Ru on the basis of salt of γ-(pyridyl)butyric acid (1), the hydrogenation of the salt of γ-(pyridyl)butyric acid (1) easily proceeds.

If the amount of the catalyst used is less than said range, the hydrogenation entails difficulty in progress, consequently tending to involve a prolonged time and possibly producing the contemplated product in a lower yield for failure to complete the reaction.

<Solvent>

The salt of γ-(pyridyl)butyric acid (1) can be hydrogenated in a solvent. Useful solvents are those capable of dissolving the salt of γ-(pyridyl)butyric acid (1) without affecting the hydrogenation thereof. For example, water is preferable for its ability to easily dissolve the salt of γ-(pyridyl)butyric acid (1) and from the viewpoints of safety and economy.

The amount of the solvent used should be in a range sufficient at least to dissolve the salt of γ-(pyridyl)butyric acid (1). For example, the amount of water used is 0.5 to 10 parts by weight, preferably 1 to 3 parts by weight, per part by weight of the salt of γ-(pyridyl)butyric acid (1).

If the amount of water used is below said range, the hydrogenation tends to involve a prolonged time because of its difficulty in the progress, and the desired product may be produced in a low yield due to incomplete reaction. The amount of water above said range raises no serious problem but leads to a low reactor efficiency. Accordingly the foregoing range is recommendable from the viewpoint of productivity.

<Reaction Conditions>

The hydrogenation can be carried out at atmospheric pressure or higher pressure, preferably a hydrogen pressure of 1 to 50 kgf/cm$^2$ (=0.1 to 5 MPa). If a Rh catalyst or a Pd catalyst is used, the hydrogenation can be efficiently conducted at a lower hydrogen pressure, e.g. 1 to 40 kgf/cm$^2$, even 1 to 30 kgf/cm$^2$.

The hydrogenation can be performed at a temperature ranging from room temperature to 140° C., preferably 40 to 120° C. A lower reaction temperature tends to extend the reaction time and is responsible for a low yield of desired product for the incomplete reaction. Hence it is undesirable. A higher reaction temperature presents no problem about the yield, but leads to a high reaction rate, making it difficult to control the temperature. Consequently said range is recommendable from the viewpoints of safety and economy.

For example, the salt of γ-(pyridyl)butyric acid (1), a catalyst and a solvent are placed into a pressure reactor equipped with a stirrer and a hydrogen inlet tube. Hydrogen is introduced through the hydrogen inlet tube with heating and stirring while the mixture is maintained at the above-mentioned hydrogen pressure and reaction temperature. Thereby the salt of γ-(pyridyl)butyric acid (1) is hydrogenated, giving the salt of γ-(piperidyl)butyric acid (2).

The salt of γ-(piperidyl)butyric acid (2) can also be produced when placing into the reactor a free γ-(pyridyl) butyric acid and an acid in place of the salt of γ-(pyridyl) butyric acid (1). This mode of process is included in the present invention.

<Purification>

The salt of γ-(piperidyl)butyric acid (2) produced by hydrogenating the salt of γ-(pyridyl)-butyric acid (1) can be easily isolated from the reaction mixture and purified by conventional methods such as crystallization or recrystallization. For example, after completion of the hydrogenation, the reaction mixture is filtered to separate the catalyst, and the solvent is distilled off. The resulting residue is subjected to recrystallization, whereby a high-purity salt of γ-(piperidyl)butyric acid (2) is isolated.

EXAMPLES

The present invention is described below in greater detail with reference to the following examples to which, however, the invention is not limited.

Example 1

A 100 ml-vol. electromagnetic agitation type autoclave (made of Hastelloy) was charged with 15.0 g (0.074 mole) of a γ-(4-pyridyl)butyric acid hydrochloride with a purity of at least 99%, 300 g of water and 0.75 g of 5% Rh/C [0.25% by weight in terms of Rh based on the γ-(4-pyridyl)butyric acid hydrochloride].

The hydrogen pressure was maintained at 5 kgf/cm$^2$ (5×10$^5$ Pa) while hydrogen was introduced, and a reaction was conducted with stirring at 110° C. for 1.5 hours. After completion of the reaction, the solvent was distilled off under reduced pressure. The residue was analyzed by high performance liquid chromatography. The analysis showed that a γ-(4-piperidyl)butyric acid hydrochloride was produced in a yield of 99%.

<Analysis conditions of high performance liquid chromatography>

Column: SHISEIDO Capcell C18 SG120 S-5 (4.6 mm (dimater)×250 mm)

Eluant: 0.02 mole/l Aqueous solution of K$_2$HPO$_4$ (adjusted to a pH of 7.0 with phosphoric acid)

Flow rate: 1.0 ml/min.

Temperature: 40° C.

Detection: UV 220 nm

Example 2

The procedure of Example 1 was repeated except the following. The same reactor as used in Example 1 was charged with 25.0 g (0.124 mole) of a γ-(4-pyridyl)butyric acid hydrochloride with a purity of at least 99%, 25.0 g of water and 1.25 g of 5% Rh/C [0.25% by weight in terms of Rh based on the γ-(4-pyridyl)butyric acid hydrochloride]. The reaction was conducted for 3 hours. A γ-(4-piperidyl) butyric acid hydrochloride was produced in a yield of 98%.

Example 3

The same procedure as in Example 1 was repeated except the following. The same reactor as used in Example 1 was charged with 13.5 g (0.067 mole) of a γ-(4-pyridyl)butyric acid hydrochloride with a purity of at least 99%, 27.0 g of water and 0.67 g of 5% Rh/C [0.25% by weight in terms of Rh based on the γ-(4-pyridyl)butyric acid hydrochloride]. The reaction was conducted at 60° C. for 8 hours. A γ-(4-piperidyl)butyric acid hydrochloride was produced in a yield of 97%.

Example 4

The procedure of Example 1 was repeated except the following. The same reactor as used in Example 1 was charged with 13.5 g (0.067 mole) of a γ-(4-pyridyl)butyric acid hydrochloride with a purity of at least 99%, 27.0 g of water and 0.67 g of 5% Pd/C [0.25% by weight in terms of Pd based on the γ-(4-pyridyl)butyric acid hydrochloride]. The reaction was conducted at 80° C. for 4.5 hours. A γ-(4-piperidyl)butyric acid hydrochloride was produced in a yield of 97%.

Example 5

The procedure of Example 1 was repeated except the following. The same reactor as used in Example 1 was charged with 13.5 g (0.067 mole) of a γ-(4-pyridyl)butyric acid hydrochloride with a purity of at least 99%, 27.0 g of water and 0.67 g of 5% Ru/C [0.25% by weight in terms of Ru based on the γ-(4-pyridyl)butyric acid hydrochloride].

The hydrogen pressure was maintained at 50 kgf/cm$^2$ (5×10$^6$ Pa) while hydrogen was introduced, and a reaction was conducted with stirring at 110° C. for 5 hours. Thereafter, the solvent was distilled off under reduced pressure. The residue was analyzed by high performance liquid chromatography. The analysis showed that a γ-(4-piperidyl) butyric acid hydrochloride was produced in a yield of 98%.

Comparative Example 1

The same procedure as in Example 1 was repeated except the following. The same reactor as used in Example 1 was charged with 15.0 g (0.091 mole) of γ-(4-pyridyl)butyric acid with a purity of at least 99%, 30.0 g of water and 0.75 g of 5% Rh/C [0.25% by weight in terms of Rh based on the γ-(4-pyridyl)butyric acid]. While hydrogen was introduced, a reaction was conducted with stirring at 110° C. for 5 hours.

The reaction involved a hydrogen pressure of 50 kgf/cm$^2$ (5×10$^6$ Pa) and produced γ-(4-piperidyl)butyric acid in a yield of 99%. At a hydrogen pressure of 5 kgf/cm$^2$ (5×10$^5$ Pa), hydrogen was slowly absorbed, making it difficult to hydrogenate the γ-(4-pyridyl)butyric acid.

Example 6

<Preparation of γ-(4-pyridyl)butyric acid hydrochloride>

A 1 liter-vol., 4-necked flask was charged with 34 g of an ethyl alcohol solution containing 20 wt % sodium ethoxide (sodium ethoxide 0.1 mole) and 240 g (1.5 moles) of diethyl malonate. A 105 g (1.0 mole) quantity of 4-vinylpyridine was added dropwise over a period of 1 hour with stirring at the reflux temperature. Then, the mixture was maintained at the reflux temperature with stirring for a further 7 hours.

After the obtained reaction mixture was cooled to room temperature, 250 g of water and 111.5 g of 36 wt % hydrochloric acid (1.1 moles) were added. After addition of 93 g of toluene, the unreacted diethyl malonate was collected as the organic layer. Then 101.4 g of 36 wt % hydrochloric acid (1.0 mole) was added to the aqueous layer. The mixture was kept at the reflux temperature with stirring for 10 hours to accomplish hydrolysis and decarboxylation.

Five grams of active carbon and 8.2 g of sellaite were added to the obtained reaction mixture. After stirring for 1 hour, the mixture was filtered. A 167 g quantity of water was distilled off from 500 g of the filtrate. The insolubles were removed by hot filtration. Then the filtrate was cooled and the crystals were separated out.

The crystals were filtered and dried, giving 97.3 g of a γ-(4-pyridyl)butyric acid hydrochloride (in a yield of 48.3% based on the 4-vinylpyridine). The obtained crystals were analyzed by high performance liquid chromatography. The analysis showed that a γ-(4-pyridyl)butyric acid hydrochloride with a purity of 98% was produced and contained about 2% of bis[2-(4-pyridyl)ethyl]acetic acid hydrochloride.

<Analysis conditions of high performance liquid chromatography>

Column: SHISEIDO Capcell C18 SG120 S-5 (4.6 mm (dimater)×250 mm)

Eluant: Aqueous solution of 0.05 wt % $K_2HPO_4$ (adjusted to a pH of 7.0 with phosphoric acid)/methyl alcohol=50/50 (volume ratio)

Flow rate: 1.0 ml/min.

Temperature: 40° C.

Detection: UV 254 nm

<Preparation of γ-(4-piperidyl)butyric acid hydrochloride>

A 100 ml-vol., electromagnetic agitation type autoclave (made of Hastelloy) was charged with 15.0 g (0.074 mole) of the above-obtained γ-(4-pyridyl)butyric acid hydrochloride, 30.0 g of water and 0.75 g of 5% Rh/C [0.25% by weight in terms of Rh based on the γ-(4-pyridyl) butyric acid hydrochloride]. While hidrogen was introduced, the hydrogen pressure was maintained at 5 kgf/cm$^2$ (5×10$^5$ Pa), and a reaction was conducted with stirring at 110° C. for 1.5 hours.

After completion of the reaction, the solvent was distilled off under reduced pressure. The residue was analyzed by high performance liquid chromatography (the same analysis conditions as in Example 1). The analysis showed that the reaction gave a γ-(4-piperidyl)butyric acid hydrochloride in a yield of 99%.

The obtained residue was recrystallized, giving 13.0 g (yield 85%) of crystals of γ-(4-piperidyl)butyric acid hydrochloride with a purity of at least 99%. The crystals contained up to 1% of bis[2-(4-piperidyl)ethyl]acetic acid hydrochloride.

Example 7

A γ-(4-piperidyl)butyric acid hydrochloride was produced by repeating the same procedure as in Example 6 except that using 0.67 g of 5% Pd/C [0.25% by weight in terms of Pd based on the γ-(4-pyridyl)butyric acid hydrochloride] in place of 5% Rh/C, a reaction was conducted at 80° C. for 4.5 hours.

The reaction gave a γ-(4-piperidyl)butyric acid hydrochloride in a yield of 97%. The obtained product was recrystallized, giving crystals of γ-(4-piperidyl)butyric acid hydrochloride with a purity of at least 99% in a yield of 90%. The crystals contained 1% or less of bis[2-(4-piperidyl) ethyl]acetic acid hydrochloride.

Example 8

<Preparation of γ-(4-pyridyl)butyric acid hydrochloride>

A 1 liter-vol., 4-necked flask was charged with 34 g (0.1 mole) of an ethyl alcohol solution containing 20 wt % sodium ethoxide and 240 g (1.5 moles) of diethyl malonate. A 105 g (1.0 mole) quantity of 4-vinylpyridine was added dropwise over a period of 1 hour with stirring at the reflux temperature. Then, the mixture was maintained at the reflux temperature with stirring for a further 7 hours.

The obtained reaction mixture was cooled to room temperature, followed by addition of 250 g of water and 111.5 g (1.1 moles) of 36 wt % hydrochloric acid. After addition of 140 g of toluene, the unreacted diethyl malonate was collected as the organic layer.

Then 220 g (1.1 moles) of 20 wt % aqueous solution of sodium hydroxide was added to the aqueous layer. After addition of 140 g of toluene, diethyl 2-[2-( 4-pyridyl)ethyl] malonate was collected as the organic layer. After distiling off the toluene from the obtained organic layer, further distillation gave 233.5 g (0.88 mole, yield 88%) of diethyl 2-[2-(4-pyridyl)ethyl]malonate.

To the obtained diethyl 2-[2-(4-pyridyl)ethyl]malonate (233.5 g) were added 220 g of water and 178.4 g (1.76 moles) of 36 wt % hydrochloric acid. Then, the mixture was maintained at the reflux temperature with stirring for 10 hours to accomplish hydrolysis and decarboxylation. After completion of the reaction, 4.4 g of active carbon and 7.2 g of sellaite were added to the reaction mixture. After stirring for 1 hour, the mixture was filtered.

The obtained filtrate was analyzed by high performance liquid chromatography (the same analysis conditions as in Example 6). The analysis showed that a γ-(4-pyridyl)butyric acid hydrochloride was produced in a yield of 99%. The filtrate contained a γ-(4-pyridyl)butyric acid hydrochloride in a concentration of 35% by weight. As to the ratio of the γ-(4-pyridyl)butyric acid hydrochloride and the bis[2-(4-pyridyl)ethyl]acetic acid hydrochloride, the former was 99% and the latter 1%.

<Preparation of γ-(piperidyl)butyric acid hydrochloride>

The same reactor as used in Example 1 was charged with 42.9 g of the above-obtained filtrate containing the γ-(4-pyridyl)butyric acid hydrochloride [15.0 g (0.074 mole) of the γ-(4-pyridyl)butyric acid hydrochloride] and 0.75 g of 5% Rh/C [0.25% by weight in terms of Rh based on the γ-(4-pyridyl)butyric acid hydrochloride].

While hydrogen was introduced, the hydrogen pressure was maintained at 5 kgf/cm$^2$ (5×10$^5$ Pa), and a reaction was conducted with stirring at 50° C. for 4 hours. After completion of the reaction, the solvent was removed under reduced pressure. The residue was analyzed by high performance liquid chromatography (the same analysis conditions as in Example 1). The analysis showed that a γ-(4-piperidyl) butyric acid hydrochloride was produced in a yield of 98%. The obtained residue was recrystallized, giving crystals of γ-(4-piperidyl)butyric acid hydrochloride with a purity of at least 99% in a yield of 90%. The crystals contained 1% or less of bis[2-(4-piperidyl)ethyl]acetic acid hydrochloride.

Comparative Example 2

The procedure of Example 7 was repeated except the following. Using 0.75 g of 5% Pt/C [0.25% by weight in terms of Pt based on the γ-(4-pyridyl)butyric acid hydrochloride] in place of 5% Rh/C, a reaction was conducted for 14 hours.

After completion of the reaction, the solvent was removed and the residue was analyzed. The analysis showed that a γ-(4-piperidyl)butyric acid hydrochloride was produced in a yield of 90% and contained 8% of the unreacted γ-(4-pyridyl)butyric acid hydrochloride.

Example 9

<Preparation of γ-(4-pyridyl)butyric acid hydrochloride>

A 1 liter-vol., 4-necked flask was charged with 34 g of an ethyl alcohol solution containing 20 wt % sodium ethoxide (sodium ethoxide 0.1 mole) and 240 g (1.5 moles) of diethyl malonate. A 105 g (1.0 mole) quantity of 4-vinylpyridine was added dropwise over a period of 1 hour with stirring at the reflux temperature. The mixture was maintained at the reflux temperature with stirring for a further 7 hours.

The obtained reaction mixture was cooled to room temperature. To the mixture were added 250 g of water and 111.5 g (1.1 moles) of 36 wt % hydrochloric acid. After addition of 140 g of toluene, the unreacted diethyl malonate was collected as the organic layer.

Then 220 g (1.1 moles) of 20 wt % aqueous solution of sodium hydroxide was added to the aqueous layer. After addition of 140 g of toluene, diethyl 2-[2-(4-pyridyl)ethyl]malonate was collected as the organic layer.

The toluene was distilled off from the obtained organic layer. To the obtained residue were added 220 g of water and 178.4 g (1.76 moles) of 36 wt % hydrochloric acid. The mixture was maintained at the reflux temperature with stirring for 10 hours to accomplish hydrolysis and decarboxylation. Then, 4.4 g of active carbon and 7.2 g of sellaite were added to the obtained reaction mixture. After stirring for 1 hour, the mixture was filtered.

The obtained filtrate was analyzed by high performance liquid chromatography (the same analysis conditions as in Example 6). The analysis showed that a γ-(4-pyridyl)butyric acid hydrochloride was produced in a yield of 92%. The filtrate contained γ-(4-pyridyl)butyric acid hydrochloride in a concentration of 32.6% by weight. As to the ratio of the γ-(4-pyridyl)butyric acid hydrochloride and the bis[2-(4-pyridyl)ethyl]-acetic acid hydrochloride, the former was 93% and the latter 7%.

<Preparation of γ-(piperidyl)butyric acid hydrochloride>

A γ-(piperidyl)butyric acid hydrochloride was produced in the same manner as in Example 8 with the exception of using the filtrate obtained above [15.0 g (0.074 mole) of the γ-(pyridyl)butyric acid hydrochloride] as one containing the γ-(pyridyl)butyric acid hydrochloride.

The reaction required 10 hours until completion. After completion of the reaction, the solvent was removed under reduced pressure and the residue was analyzed by liquid chromatography in the same manner as in Example 1. The analysis showed that a γ-(4-piperidyl)butyric acid hydrochloride was produced in a yield of 98%. The obtained residue was recrystallized, giving crystals of γ-(4-piperidyl)butyric acid hydrochloride with a purity of 93.5% in a yield of 83%. The crystals contained 6.5% of bis[2-(4-piperidyl)ethyl]acetic acid hydrochloride.

What is claimed is:

1. A process for preparing a salt of γ-(piperidyl)butyric acid with an acid, the salt being represented by the formula (2)

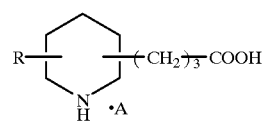

wherein R is a hydrogen atom or an alkyl group, and A is an acid, the process comprising the step of hydrogenating a salt of γ-(pyridyl)butyric acid with an acid, the salt being represented by the formula (1)

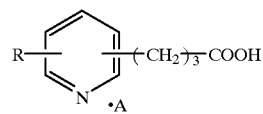

wherein R and A are as defined above in a solvent in the presence of a catalyst, the process being characterized in that the catalyst is a Rh catalyst, a Pd catalyst or a Ru catalyst.

2. The process according to claim 1, wherein the salt of γ-(pyridyl)butyric acid with an acid, the salt being represented by the formula (1) is prepared by carrying out the undermentioned steps (a) and (b) and contains not more than 3% by weight of a salt of bis(pyridylethyl)acetic acid with an acid, the salt being represented by the formula (3)

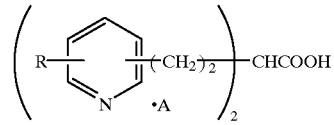

wherein R and A are as defined in claim 1:

(a) reacting a vinylpyridine compound represented by the formula (4)

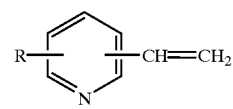

wherein R is as defined in claim 1 with a diester of malonic acid represented by the formula (5)

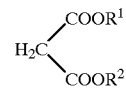

wherein $R^1$ and $R^2$ are the same or different and each represents an alkyl group in the presence of a base to give a diester of 2-(pyridylethyl)malonic acid represented by the formula (6)

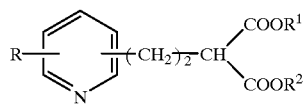
(6)

wherein R is as defined in claim 1, and $R^1$ and $R^2$ are as defined above and;

(b) hydrolyzing and decarboxylating the diester of 2-(pyridylethyl)malonic acid of the formula (6) prepared in the step (a) in an acidic aqueous solution to give the salt of γ-(pyridyl)butyric acid with an acid, the salt being represented by the formula (1).

3. The process according to claim 1 or 2, wherein the catalyst is Rh/C, Pd/C or Ru/C.

4. The process according to claim 1 or 2, wherein the amount of the catalyst used is 0.05 to 0.3% by weight in terms of a metal (Rh, Pd or Ru) based on the salt of γ-(pyridyl)butyric acid with an acid.

5. The process according to claim 1 or 2, wherein the salt of γ-(pyridyl)butyric acid with an acid is hydrogenated at a hydrogen pressure of 1 to 50 kgf/cm$^2$.

6. The process according to claim 1 or 2, wherein the catalyst of a Rh catalyst or a Pd catalyst.

7. The process according to claim 6, wherein the catalyst is Rh/C or Pd/C.

8. The process according to claim 6, wherein the amount of the catalyst used is 0.05 to 0.3% by weight in terms of a metal (Rh or Pd) based on the salt of γ-(pyridyl)butyric acid with an acid.

9. The process according to claim 6, wherein the salt of γ-(pyridyl)butyric acid with an acid is hydrogenated at a hydrogen pressure of 1 to 40 kgf/cm$^2$.

10. The process according to claim 3, wherein the amount of the catalyst used is 0.05 to 0.3% by weight in terms of a metal (Rh, Pd or Ru) based on the salt of γ-(pyridyl)butyric acid with an acid.

11. The process according to claim 7, wherein the amount of the catalyst used is 0.05 to 0.3% by weight in terms of a metal (Rh or Pd) based on the salt of γ(pyridyl)butyric acid with an acid.

\* \* \* \* \*

UNITED STATES PATENT AND TRADEMARK OFFICE
CERTIFICATE OF CORRECTION

PATENT NO.   : 6,197,961 B1
DATED        : March 6, 2001
INVENTOR(S)  : Sakai et al.

It is certified that error appears in the above-identified patent and that said Letters Patent is hereby corrected as shown below:

Title page,
Item [86], change the § 371Date and § 102(e) Date, "January 4, 1998" to be -- June 4, 1998 --

Signed and Sealed this

Fourth Day of December, 2001

*Attest:*

NICHOLAS P. GODICI
*Acting Director of the United States Patent and Trademark Office*

*Attesting Officer*